(12) United States Patent  
O'Connell

(10) Patent No.: US 8,194,243 B2  
(45) Date of Patent: Jun. 5, 2012

(54) CELL TRAY

(75) Inventor: Daniel G. O'Connell, Kihei, HI (US)

(73) Assignee: Nanopoint, Inc., Honolulu, HI (US)

( * ) Notice: Subject to any disclaimer, the term of this patent is extended or adjusted under 35 U.S.C. 154(b) by 139 days.

(21) Appl. No.: 12/280,788

(22) PCT Filed: Feb. 27, 2006

(86) PCT No.: PCT/US2006/006868  
§ 371 (c)(1),  
(2), (4) Date: Dec. 10, 2008

(87) PCT Pub. No.: WO2007/097761  
PCT Pub. Date: Aug. 30, 2007

(65) Prior Publication Data  
US 2009/0221023 A1   Sep. 3, 2009

(51) Int. Cl.  
*G01N 1/10* (2006.01)

(52) U.S. Cl. ......................................................... 356/246

(58) Field of Classification Search .................... 356/246  
See application file for complete search history.

(56) References Cited

U.S. PATENT DOCUMENTS

| | | | | |
|---|---|---|---|---|
| 4,231,660 A | * | 11/1980 | Remy et al. | 356/244 |
| 4,237,234 A | * | 12/1980 | Meunier | 356/246 |
| 4,415,405 A | | 11/1983 | Ruddle et al. | |
| 4,729,949 A | * | 3/1988 | Weinreb et al. | 356/244 |
| 6,238,911 B1 | | 5/2001 | Kasahara | |
| 6,519,032 B1 | | 2/2003 | Kuebler et al. | |
| 6,980,293 B1 | * | 12/2005 | Harada | 356/246 |
| 2002/0064809 A1 | * | 5/2002 | Mutz et al. | 435/40.5 |
| 2002/0155617 A1 | * | 10/2002 | Pham et al. | 356/246 |
| 2002/0173033 A1 | * | 11/2002 | Hammerick et al. | 435/305.2 |
| 2003/0020915 A1 | | 1/2003 | Schueller et al. | |
| 2005/0014201 A1 | * | 1/2005 | Deuthsch | 435/7.2 |
| 2005/0047971 A1 | | 3/2005 | Clements et al. | |
| 2005/0280811 A1 | * | 12/2005 | Sandell | 356/246 |

OTHER PUBLICATIONS

PCT International Search Report and Written Opinion of the International Searching Authority, issued Aug. 15, 2006, application No. PCT/US06/006868.

* cited by examiner

*Primary Examiner* — Kara E Geisel  
(74) *Attorney, Agent, or Firm* — Convergent Law Group LLP

(57) ABSTRACT

A cell tray has a multi-dimensional array of cells in precise, equally spaced wells (cubicles or silos) containing medium of interest. The ordered cell array enables automated processing as well as simultaneous monitoring and analyzing of a large matrix of cells, biological fluids, chemicals and/or solid samples. The invention is an integrated device and is fabricated into substrates similar to microscope slides. The ordered array of cells in precise locations helps in parallel analysis and processing of cells simultaneously. Each cell cubicle or silo in the array is located equidistant from its nearest neighbors in an orthogonal direction. The location of each well can be precisely measured and recorded in an automated processing system. Included in the bottom of each cell well is an optional micro-lens. An array of probes provides parallel cell processing and monitoring capabilities, including microinjection and microscope analysis.

15 Claims, 6 Drawing Sheets

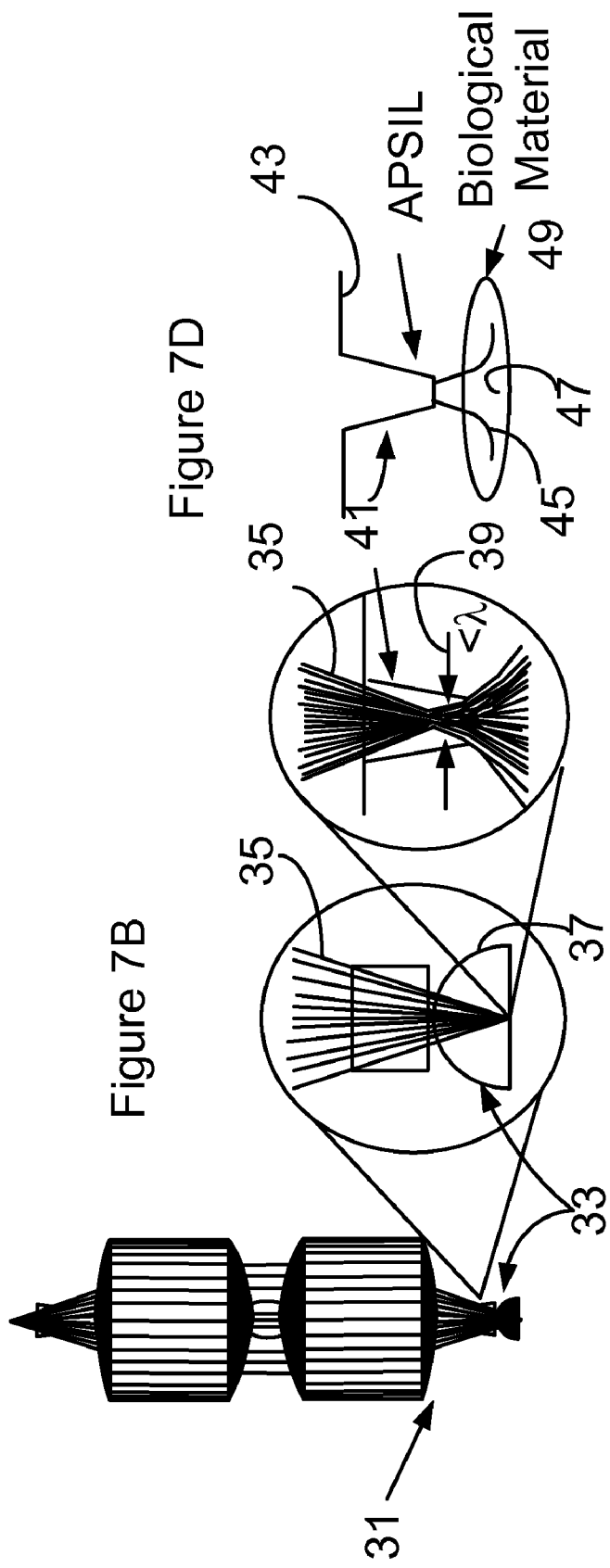

CELL TRAY

CROSS-REFERENCE TO RELATED APPLICATIONS

This application claims is a National Stage under 35 U.S.C. 371 of International Patent Application No. PCT/US2006/006868, filed on Feb. 27, 2006, and is related to U.S. Provisional Application No. 60/431,566, filed Oct. 28, 2002 and U.S. patent application Ser. No. 10/290,528 filed Nov. 8, 2002.

BACKGROUND OF THE INVENTION

Current methods of cell analysis involve living cells cultured in petri dishes, well plates and on microscope slides. These previous methods of culturing live cells suffer from inconsistent arrangement of cells and slow processing times. The arrangement of the cells in previous cell analysis methods is random, with areas of high cell congregation and other regions where cells are sparsely distributed.

Biological research laboratories and biological instrument and supply companies are constantly looking for new methods to make cell analysis more efficient.

Needs exist for improved simultaneous multiple cell analysis, observation and cell injections.

SUMMARY OF THE INVENTION

The present invention preferably has a two-dimensional array of cells in precise, equally spaced rectangular cubicles or cylindrical silos (otherwise referred to individual cell wells) that contain life support medium. The ordered cell array enables automated processing as well as simultaneous monitoring and analyzing of a large matrix of cells, biological fluids, chemicals and/or solid samples. The present invention is an integrated device and is fabricated into substrates similar to microscope slides used for conventional microscope viewing or spectroscopic studies The present invention provides a method of containing an ordered array of cells in precise locations for use in parallel analysis and processing of cells simultaneously. Each cell well, in the square array, is located equidistant from its nearest neighbors in an orthogonal direction. The location of each well can be precisely measured and recorded in an automated processing system. Included in the bottom of each cell well are micro-optic lenslets or micro-machined diffractive optic lenses as an optional feature to provide additional resolution when combined with conventional microscope or to enhance the POINT microscope, or other instrumentation. An array of probes provides parallel cell processing and monitoring capabilities, including microinjection and microscope analysis.

The present invention works well with the Precision Optical Intracellular Near Field Imaging/Spectroscopy Technology (POINT or NANOPOINT) invention described in co-pending patent application Ser. No. 10/290,528 which is incorporated herein by reference in its entirety.

POINT is a novel high-resolution instrument for analyzing and comparing molecular characteristics of cells. Currently, confocal microscopes, MRI and ultrasound cannot image to a 50 nm resolution and the use of electron microscopes destroys the cells. The POINT system is a nanosensor array capable of imaging inner regions of living cells without destroying its natural environment. The system uniquely provides new information about the molecular makeup of a cell.

The POINT system is not limited to just imaging inside living cells but it is also useful for any application where sub-wavelength resolution is important. Another application of the POINT system is to observe gene expression in cells.

POINT is a near-field microscope imaging system that converts any conventional microscope to have near-field capability. The POINT microscope stage may be installed on most conventional microscopes and may also be transported between microscopes. The new microscope stage has specialized controllers to maneuver the solid immersion lens or fiber-optic probe and control the distance to the sample to sub-wavelength proximity.

This new microscope houses either an array of fiber probes or a solid immersion lens, which accepts a high numerical aperture beam from a high NA objective within a conventional microscope. The solid immersion lens reduces the wavelength in the glass thereby forming a smaller light spot at its internal focus. POINT combines a multiple aperture near-field probe array with the cell tray enabling multiple live cell processing with sub-wavelength resolution imagery and spectroscopy.

The POINT microscope is suitable for imaging living biological samples using a technique that accommodates large-scale production. The POINT near-field microscope platform may be interfaced with most conventional laboratory light microscopes thus making near-field available to a vast research community.

The POINT system may be applied to near field optical microscopy applications as a research tool for medical and biological imaging as well as medical diagnostics as an early warning device for detection of diseased cells and to aid in drug development and treatments. POINT technology can be used to transform an existing microscope into a high resolution nanoscope.

In addition to use in analysis and processing of living cells, the present invention is also useful in analysis and processing of other fluid or solid samples.

These and further and other objects and features of the invention are apparent in the disclosure, which includes the above and ongoing written specification, with the claims and the drawings.

BRIEF DESCRIPTION OF THE INVENTION

FIG. 7A shows an solid immersion lens (SIL) microscope configuration.

FIG. 7B is an enlarged view of a solid immersion lens.

FIG. 7C is an enlarged view of the near-field aperture probe.

FIG. 7D is a near-field illumination of a cell.

DETAILED DESCRIPTION OF THE PREFERRED EMBODIMENTS

The present invention provides a method of containing an ordered array of cells 1 in precise locations for use in parallel analysis and processing of cells 5 simultaneously.

Figure 1:
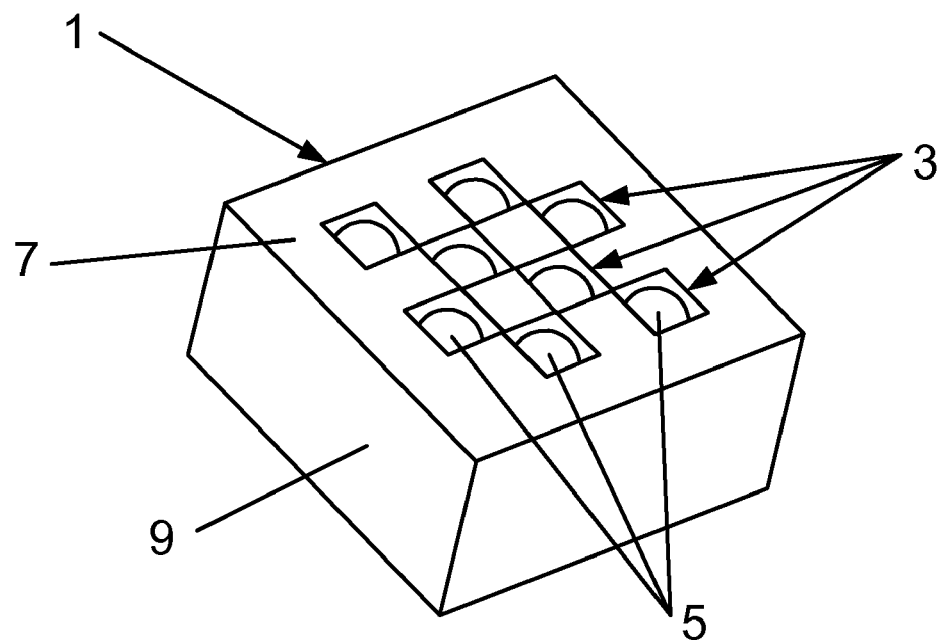
FIG. 1 is a schematic of the cell tray.

As shown in FIG. 1, each cell cubicle or silo 3, in the square cell array 1, is located equidistant from its nearest neighbors in an orthogonal direction.

The cell tray 1 is fabricated using micro-machining techniques. A layer of chrome is deposited onto the cell carrier substrate 9. A layer of photoresist 7 is spin coated over the chrome. The material for the cell carrier substrate 9 includes, but is not limited to, fused silica (quartz), soda-lime glass, silicon, germanium, sapphire, and plastic. Other base substrates are used depending on the desired optimal transmission properties in various parts of the electromagnetic spectrum.

A lithographic mask is designed on computer and directly written on the photoresist with a laser scanning microscope. Alternatively a two-axis Ronchi ruling is used to expose a crossed-grating pattern on the photoresist layer 7. Alternatively a lithographic shadow mask may be substituted for the Ronchi grating. The shadow mask consists of a two-dimensional array of square or circular apertures to optimize performance in different applications. A holographic exposure process may also be used to generate a crossed-grating interference pattern in the photoresist.

The photoresist 7 is exposed using laser light or broadband white light. Regions in the photoresist 7 that were in shadow and not exposed remain as surface structure in the photoresist after the developing process (the opposite structure would result from negative photoresist). A two-dimensional ordered array of square, circular or other geometric shaped regions is removed during a developing process.

The fabrication process is not limited to negative or positive photoresist 7 processes. A positive photoresist 7 can be substituted along with a negative of the aperture mask. In addition the cell cubicles or silos 3 can be fabricated using e-beam or deep UV lithography in PMMA substrate or any other optical substrate. The substrate 9 may be any material chosen based on its optical and mechanical properties including, but not limited to, soda lime glass, borosilicate glass, Fused Silica, PMMA, Sapphire, Silicon or Germanium. The cell containment features including fluid channels and micro-optic lenses can be produced using hot press, embossing or stamping on suitable glass or plastic substrates.

The exposed chrome regions are removed with a liquid chemical etch. The remaining photoresist can then be removed resulting in a metallic mask outline of the desired pattern. The substrate 9 is processed using a reactive ion etching procedure. The etch process results in features etched or transferred into the cell tray base substrate 9 without affecting the chrome layer.

Figure 2:
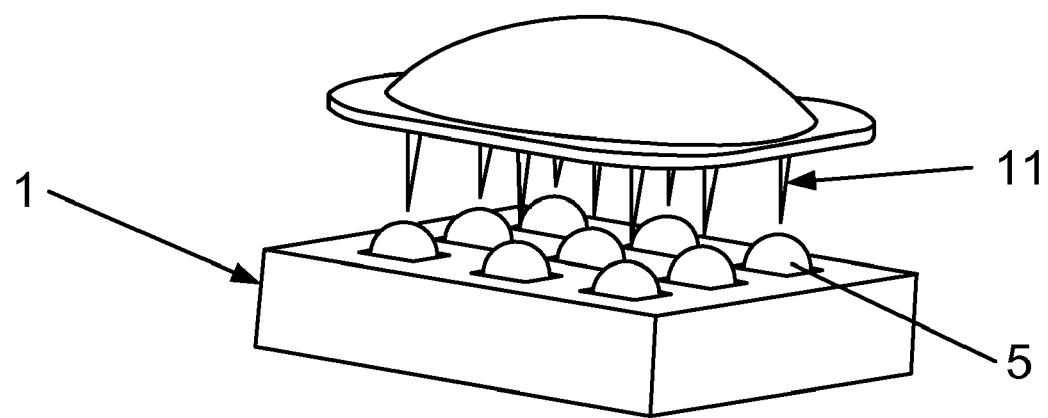
FIG. 2 is a diagram of the cell tray with a probe array.

As shown in FIG. 2, the cell tray 1 can be used for parallel processing and analysis of cells simultaneously, using an array of probes 11 that are fabricated with spacing identical to the cell cubicles 3. The present invention provides added capability for parallel cell processing and monitoring, including microinjection and microscope analysis.

Figure 3:
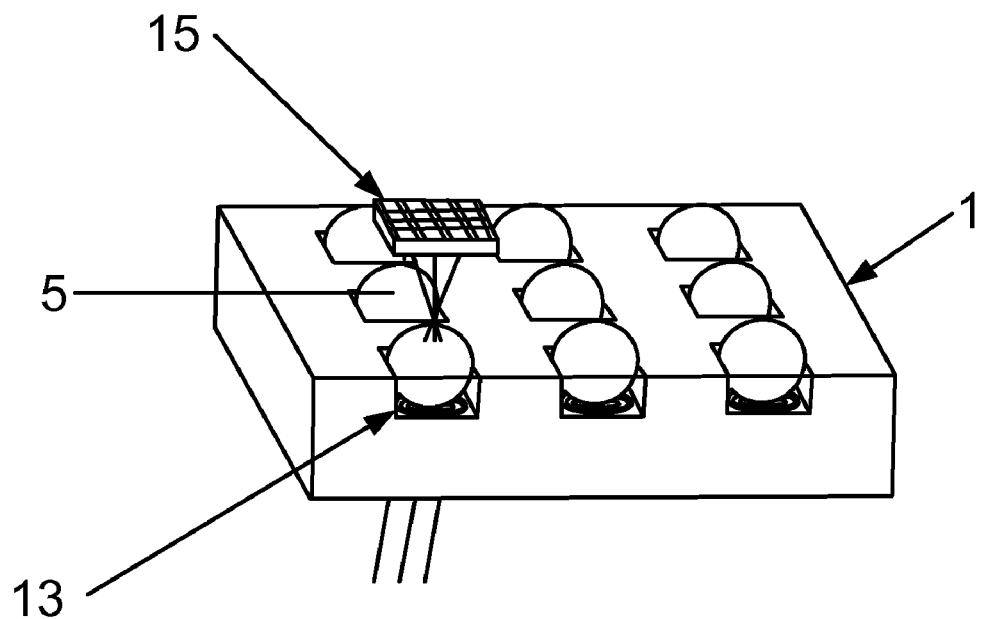
FIG. 3 is a diagram of the cell tray integrated with a microscope objective lens array.

Referring to FIG. 3, the cell tray 1 incorporates an optional micro-optical lens element 13 situated at the base of each cell cubicle 3. The micro-lens 13 provides microscopic imaging and analysis, for example using solid and liquid immersion optical techniques for high-resolution imaging. The micro-optic lens (diffractive, refractive or holographic) lens 13 is produced as an integrated part of the cell tray 1 during the same micro-machining (or embossing, stamping or pressing) process that generates the cell cubicles 3. For example a Fresnel type lens structure 13 is produced at the base of the well 3, with a binary transmittance or grayscale mask, as well as a phase mask or kinoform. The cell tray 1 may be integrated with a microscope objective lens array 15 above the sample cell 5.

Figure 4:
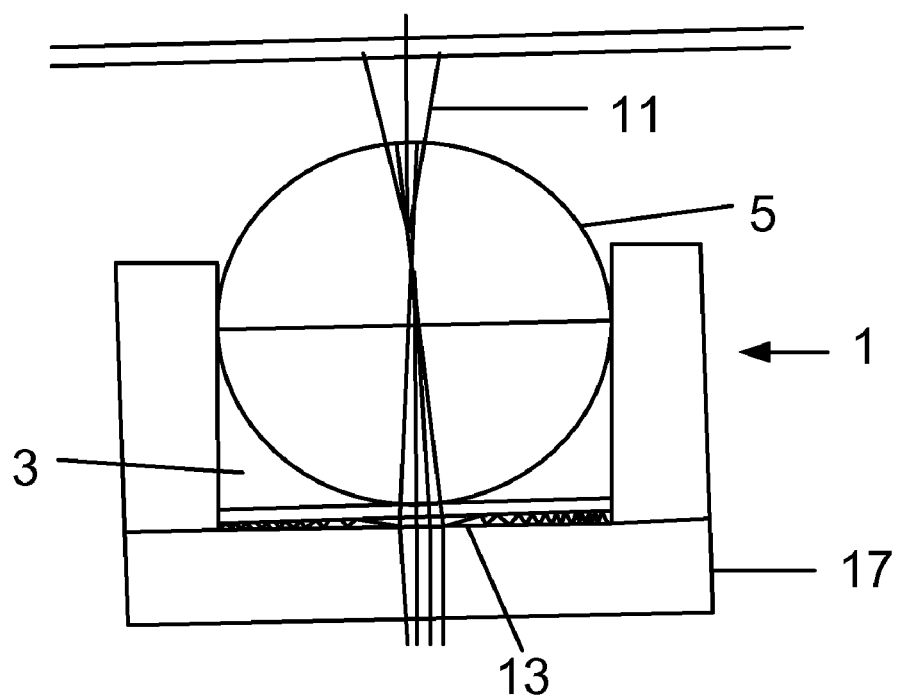
FIG. 4 is a schematic of the cell tray with a cell probe and Fresnel lens.

As shown in FIG. 4, a two-dimensional array 1 of cubicles or silos 3 are machined into an optical or other substrate 9 for multiple cell analysis, or the analysis of fluid or solid samples simultaneously. The cell tray 1 can be mounted onto an invar backing plate 17, with a clear aperture for viewing transmission. The invar 17 or another material is used as mechanical support to maintain a uniform flat surface of the cell tray 1. This may be beneficial when the Cell Tray is fabricated in a thin glass wafer similar in dimensions to a microscope cover slip.

The cell tray 1 may contain any number of cell cubicles 3 in a linear array or precisely determined two-dimensional array 1 and is limited only by the size of the substrate 9 and the ion beam in the reactive ion etching camber. The lateral dimensions of the cubicles and depth can vary between cell tray devices and is not limited to a single fixed dimension.

The precise arrangement of the cell wells 3 enables multiple cell analysis and processing simultaneously, which is currently not possible. This invention increases the speed of cell analysis, as well as provides new techniques for monitoring cell and other samples under a variety of conditions.

Figure 5:
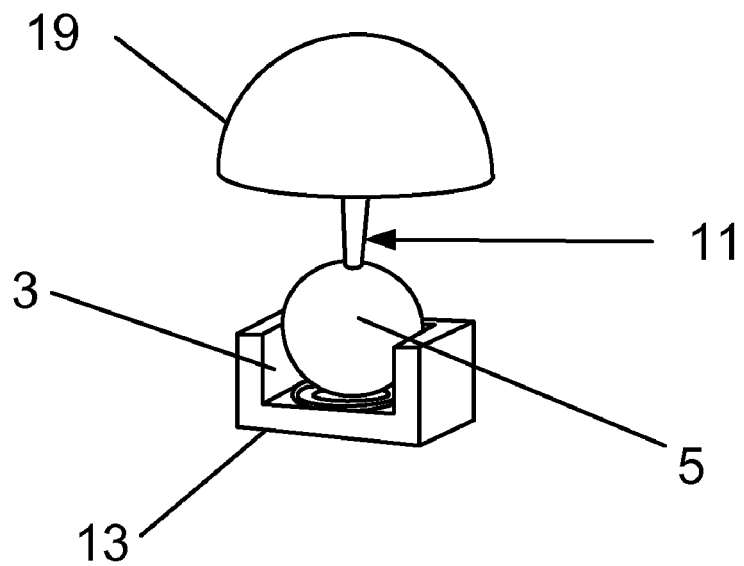
FIG. 5 is view of the cell tray interfacing with the automated system for cell monitoring.

As shown in FIG. 5, each cell well 3 is indexed by an automation system 19 for cell monitoring and processing. The array of cell cubicles 3 provides for the simultaneous collection of light for imaging, and spectroscopy of samples in multiple regions of the spectrum.

The cell tray 1 of the present invention is machined into conventional microscope slides or cover slips, as well as other optical substrates. The cell tray system 1 is used in both transmission or reflection mode microscopes and spectrometer configurations in the ultraviolet, visible and infrared regions of the electromagnetic spectrum.

Figure 6:
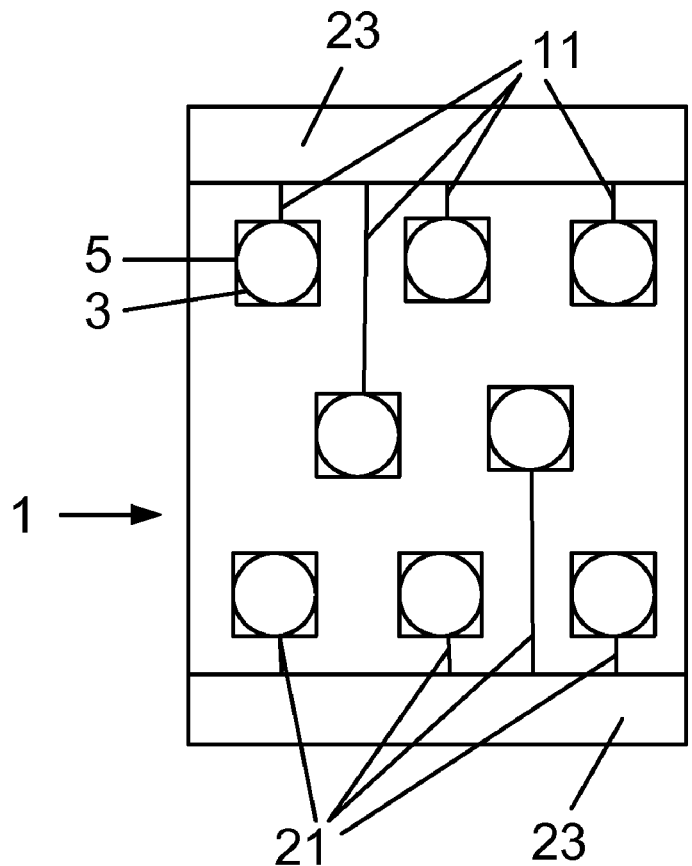
FIG. 6 is a top view of the cell tray with a fluid delivery system and fluid channels.

As shown in FIG. 6, an integrated network of micro-channels 21 can be etched into the substrate 9 to provide fluid delivery to each cell well 3. Similar to forming wire traces in an integrated circuit, a network of fluid channels 21 can be etched into the substrate 9 using photolithography transfer process or shadow mask. Each cell well 3 has a dedicated fluid delivery channel 21 that extends from the cell well 3 to the edge of the optical substrate 9 or wafer and attached to a fluid delivery manifold 23. This allows different drug agents, chemicals of different concentration or pH, dyes or any liquid to be delivered via a fluid channel 21 to each cell well 3. This integrated micro-optic chip on an optical wafer enables parallel processing and analysis of a large number of cells as well as precise and regulated drug delivery or other fluid delivery processes. The present invention also enables the rapid analysis of a large number of living cells for various experiments in cancer and other disease research and drug development. The present invention enables flow analysis of live cells with canals that are wide channels that run across the length or width of the cell tray. These canals enable live cells to flow across the wafer to enable cell counting, cell size measurement and other live cell parameters.

FIGS. 7A-7D show a solid immersion lens with near-field aperture. FIG. 7A is a microscope/SIL combination 31. FIG. 7B is an enlarged view of the SIL 33, illustrating the incoming rays 35 normal to the convex side 37 of the SIL 33. FIG. 7C is an enlarged view of the near-field aperture probe 41. A computer model shows light rays 35 focusing halfway 39 through the near-field probe 41 placed at the base 43 of the SIL 33. FIG. 7D shows the near-field illumination 45 of a cell 47 in biological material 49.

Figure 8A:
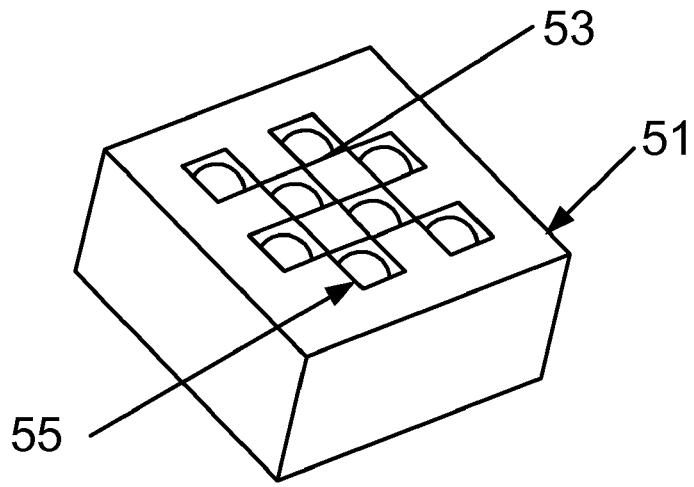
FIG. 8A shows the "Cell Tray" holding individual cells stationary in a precise array.
Figure 8B:
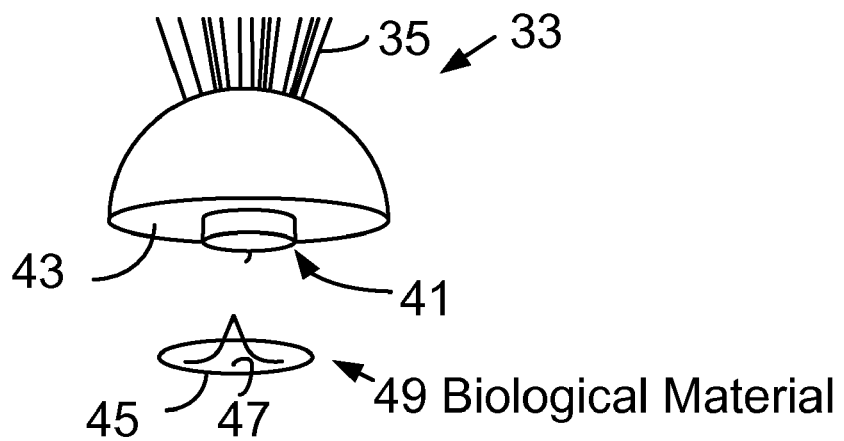
FIG. 8B shows a near-field probe technique using the probe at the base of an SIL.
Figure 8C:
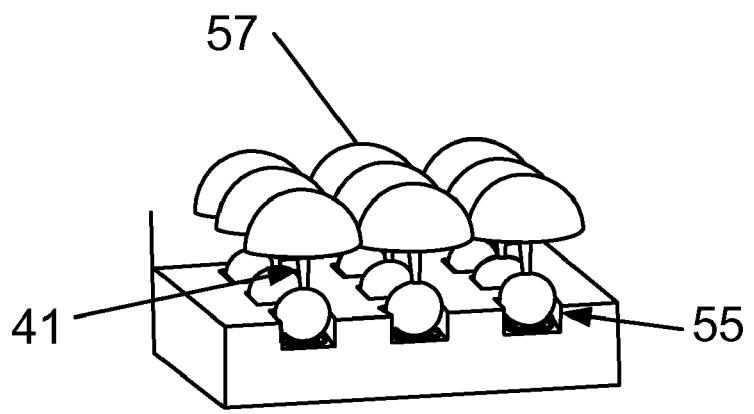
FIG. 8C is a diagram of multiple probes fabricated in combination with a cell well array.

FIG. 8A shows cell tray 51. The cell tray is a cell containment system 51 for holding individual cells 53 stationary in a precise array 55. FIG. 8B shows a near-field probe technique using the probe 41 at the base 43 of the SIL 33. FIG. 8C is a diagram of multiple probes 41 fabricated in combination with a cell well array 55.

Figure 9:
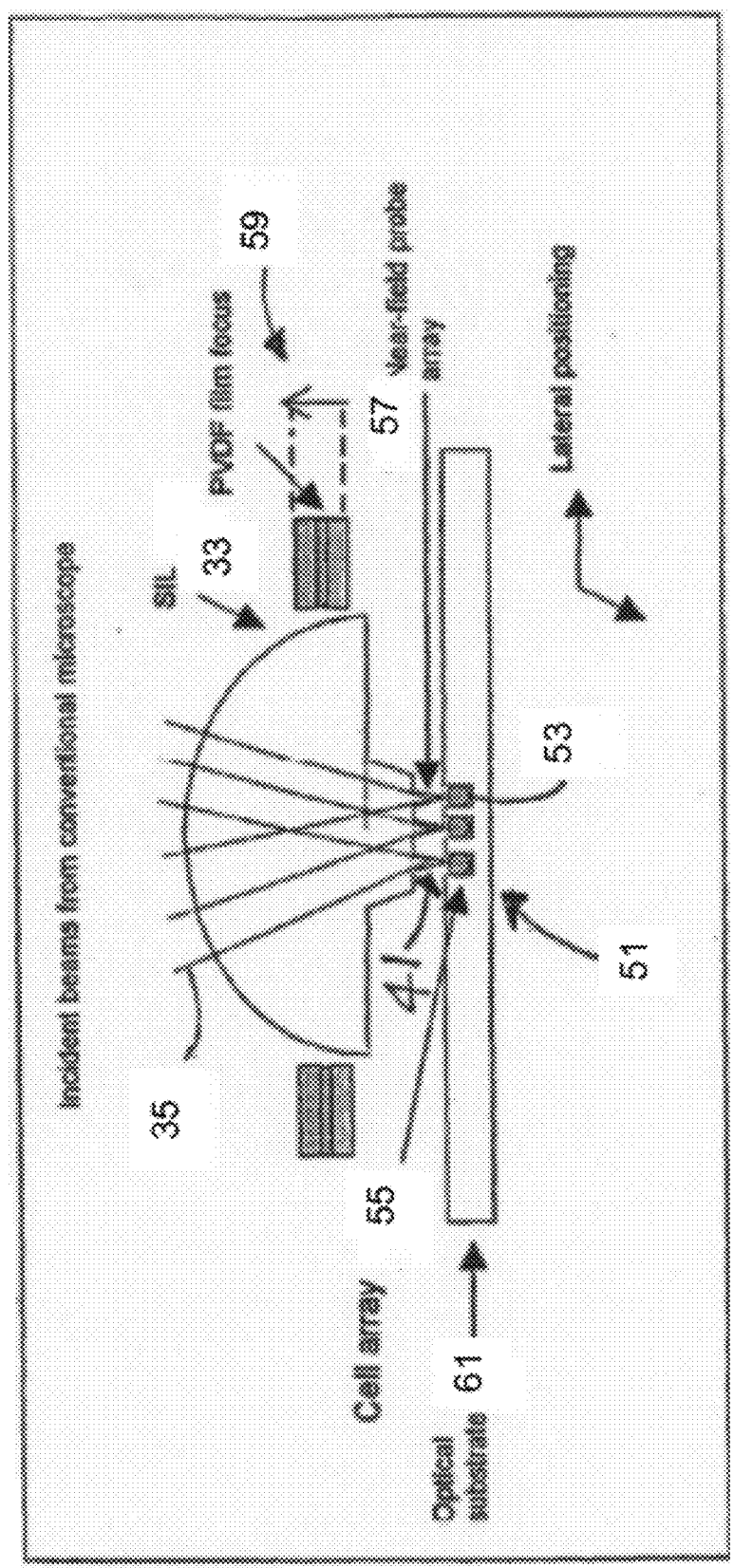
FIG. 9 shows the integrate POINT system including an array of near-field probes.

FIG. 9 shows the integrate POINT system including a probe array 57 of near-field probes 41 for intra-cellular imaging with sub-wavelength resolution imaging and spectroscopy 59 coupled with a precision focus control device and cell containment system 51.

Because of the unique configuration of the POINT system, direct viewing of cells and other biological material is possible. This is not the case with commercially available near-field scanning optical microscopes (NSOM). Until now, near-field probes were designed to move over the surface of the object being measured. The present invention uniquely provides a technique to penetrate the cell membrane with a near-field probe and to image the inside of an intact cell without destroying the cell structure. The POINT platform has many applications, including but not limited to, biomedical imaging, surface metrology and chemistry at the nanoscale.

The POINT invention, described in co-pending patent application Ser. No. 10/290,528, is incorporated herein by reference in its entirety. The POINT system encompasses an array of near-field probes which may consist of either an array of fiber probes or an array of probes formed at the base of a solid immersion lens for biological imaging which provides greater light throughput. POINT has the capability of simultaneously collecting image data and spectroscopy information in the vicinity of the near-field probes by combining multiple techniques such as fluorescence, Raman, and absorption spectroscopy. Producing a beam diameter only nanometers in size enables spectroscopy to be performed in a very small cross-section. There is an increase in optical efficiency when coupling light through a sub-wavelength aperture using a solid immersion lens.

Forming many probes in an array essentially provides a multiple aperture near-field microscope. This creates a means of analyzing multiple cells at once or multiple image points within a sample. The probe array combined with the cell tray, which contains a number of cells or other samples in a regular array of "buckets," provides a unique tool for cell analysis.

Using lithography techniques, the near-field microscope is fashioned with an array of probes with precisely the same period in two-dimensions as the cell tray. Multiple cells are then analyzed in an ordered fashion. The invention allows for efficient monitoring of cell activity including, but not limited to, response to drugs, protein content, gene expression, and the like, and enables each cell to be treated differently. The probe array may be built into a computerized stage for certain automated functions. Each cell well of interest can be precisely aligned to the near-field probe array.

This new probe works very well for cell penetration, which is applied as an array of near-field probes in an optical substrate. The geometry of the probe is easily determined from a series of cell poking experiments and light throughput measurements.

While the invention has been described with reference to specific embodiments, modifications and variations of the invention may be constructed without departing from the scope of the invention, which is defined in the following claims.

The invention claimed is:

1. A cell containment apparatus comprising:
   a cell tray including a substrate;
   a two-dimensional array of cell wells on the substrate and a medium, each cell well of the two-dimensional array of cell wells configured to retain a single living cell substantially in place, the medium including the single living cell disposed in each cell well of the cell wells, each cell well further including a micro-lens element integrated into the substrate; and
   a plurality of microchannels in the substrate, the plurality of microchannels allowing fluid access to the plurality of cell wells, the two-dimensional array of cell wells, the plurality of microchannels and the micro-lens element being integrated into the substrate.

2. A method for analyzing a property of a living cell, comprising:
   providing a cell tray including a substrate, a two-dimensional array of cell wells on the substrate, a plurality of microchannels in the substrate, and a medium, each cell well of the two-dimensional array of cell wells configured to retain a single living cell substantially in place and including a micro-lens element integrated into the substrate, the medium including the single living cell disposed in each of the cell wells, the plurality of microchannels allowing fluid access to the plurality of cell wells, the two-dimensional array of cell wells, the plurality of microchannels and the micro-lens element being integrated into the substrate;
   supporting the single living cell in each of the cell wells during a period of analysis; and
   determining the property of the single living cell by performing a process selected from the group consisting of observing the single living cell, monitoring the single living cell, analyzing a biological fluid related to the single living cell, analyzing the medium including the single living cell, imaging the single living cell, performing spectroscopic analysis of the medium including the single living cell, performing flow analysis of the single living cell, imaging an inside of an intact single living cell, and monitoring cell activity.

3. The apparatus of claim 1, wherein the substrate is an optical substrate.

4. The apparatus of claim 3, wherein the optical substrate is formed from a material selected from the group consisting of fused silica, soda lime glass, borosilicate glass, PMMA, sapphire, silicon, and germanium.

5. The apparatus of claim 1, wherein the cell tray is formed as a microscope slide.

6. The apparatus of claim 1, wherein each cell well on the substrate is formed as a square, optionally having one or more rounded corners, the square having a side length substantially equal to a diameter of a cell.

7. The apparatus of claim 1, wherein the medium further comprises a component selected from the group consisting of a life support medium for the living cells, a biological fluid, a drug, a chemical and an analyte.

8. The apparatus of claim 1, further comprising microchannels in the substrate interconnecting the cell wells for delivery of a fluid to the cell wells.

9. The apparatus of claim 8, further comprising a delivery manifold and a set of fluid channels on the substrate in fluid communication with the delivery manifold and in fluid communication with the micro-channels for delivery of the fluid into the cell wells.

10. The method of claim 2, wherein the substrate includes an integrated micro-optic chip on an optical wafer substrate for parallel processing and analysis of a large number of the cell wells, and wherein the method further comprises regulating and precisely delivering a preselected substance to each of the cell wells.

11. The method of claim 2, wherein the medium further includes a component selected from the group consisting of a life support medium for the single living cell living cell, a biological fluid, a drug, a chemical, a dye, and an analyte.

12. The method of claim 2, further comprising:
    indexing each cell well to be used with an automation system, and determining the property of the single living cell using the automation system.

13. A process for fabricating a cell containment device comprising:
    forming a cell tray with a substrate;
    forming a two-dimensional array of cell wells on the substrate, each of the cell wells configured to retain a single cell substantially in place, each cell well further including a micro-lens element integrated into the substrate; and
    forming a plurality of microchannels in the substrate, the plurality of microchannels allowing fluid access to the plurality of cell wells, the two-dimensional array of cell wells, the plurality of microchannels and the micro-lens element being integrated into the substrate.

14. The process of claim 13, wherein the substrate is formed from a material selected from a group consisting of fused silica, soda lime glass, borosilicate glass, PMMA, sapphire, silicon, and germanium.

15. The process of claim 13, further comprising:
    etching an integrated network of micro-channels into the substrate.

* * * * *